US012577341B2

(12) United States Patent
Wang et al.

(10) Patent No.: US 12,577,341 B2
(45) Date of Patent: Mar. 17, 2026

(54) COPOLYMER DERIVED FROM SUBSTITUTED BENZOPINACOL AND USE OF THE SAME AS POLYMERIZATION INITIATOR

(71) Applicant: BASF COATINGS GMBH, Münster (DE)

(72) Inventors: Ming Wang, Shanghai (CN); Ling Yu Sui, Shanghai (CN); Na Liu, Shanghai (CN); Shrirang Hindalekar, Navi Mumbai (IN); Mushtaq Patel, Navi Mumbai (IN); Rahul Mulay, Navi Mumbai (IN); Qin Yuan Chen, Shanghai (CN); Yang Yang, Shanghai (CN)

(73) Assignee: BASF COATINGS GMBH, Muenster (DE)

( * ) Notice: Subject to any disclaimer, the term of this patent is extended or adjusted under 35 U.S.C. 154(b) by 481 days.

(21) Appl. No.: 18/043,760

(22) PCT Filed: Aug. 24, 2021

(86) PCT No.: PCT/EP2021/073385
§ 371 (c)(1),
(2) Date: Mar. 2, 2023

(87) PCT Pub. No.: WO2022/048951
PCT Pub. Date: Mar. 10, 2022

(65) Prior Publication Data

US 2023/0312793 A1 Oct. 5, 2023

(30) Foreign Application Priority Data

Sep. 4, 2020 (WO) ................ PCT/CN2020/113552

(51) Int. Cl.
*C08F 236/20* (2006.01)
*C07C 69/78* (2006.01)
*C08K 5/101* (2006.01)

(52) U.S. Cl.
CPC ............ *C08F 236/20* (2013.01); *C07C 69/78* (2013.01); *C08K 5/101* (2013.01)

(58) Field of Classification Search
None
See application file for complete search history.

(56) References Cited

U.S. PATENT DOCUMENTS

| | | | | |
|---|---|---|---|---|
| 4,288,527 | A | 9/1981 | Morgan | |
| 4,535,174 | A | 8/1985 | Crivello | |
| 8,487,054 | B2 | 7/2013 | Murray et al. | |
| 2005/0009992 | A1 | 1/2005 | Voorheis | |
| 2013/0190467 | A1* | 7/2013 | Murray .................. | C08K 5/053 526/170 |

OTHER PUBLICATIONS

International Search Report and Written Opinion for corresponding PCT/EP2021/073385 mailed Nov. 29, 2021, 12 pages.

* cited by examiner

*Primary Examiner* — Satya B Sastri
(74) *Attorney, Agent, or Firm* — Armstrong Teasdale LLP

(57) ABSTRACT

Disclosed herein is a copolymer, including (A) allyloxycarbonyl substituted benzopinacol monomer of formula (I) and (B) at least one ethylenically unsaturated monomer, in copolymerized form. Also disclosed herein is a use of the copolymer as a radical polymerization initiator. Further disclosed herein is the allyloxycarbonyl substituted benzopinacol monomer of formula (I).

20 Claims, 1 Drawing Sheet

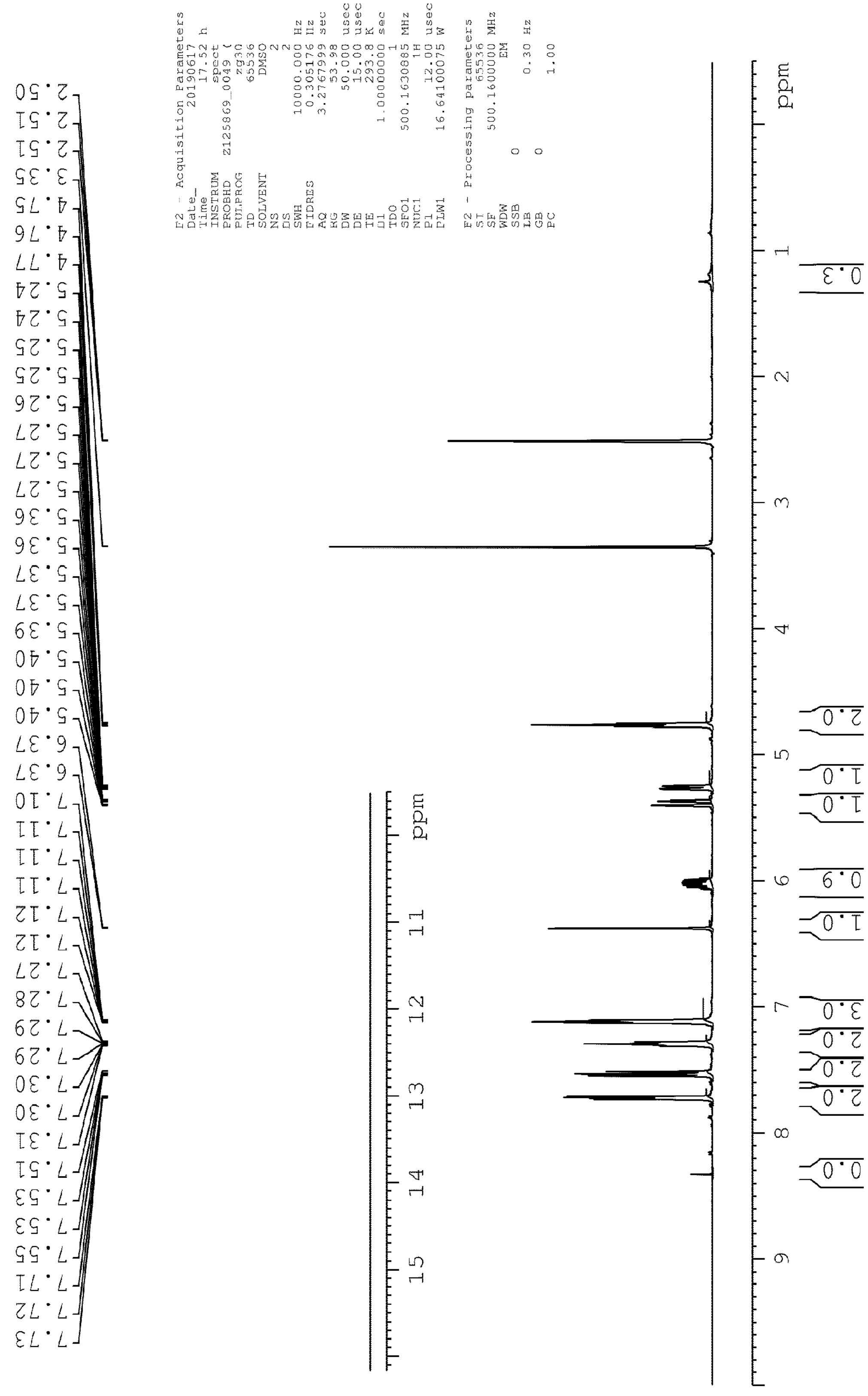
F2 - Acquisition Parameters
Date_ 20190617
Time 17.52 h
INSTRUM spect
PROBHD Z125869_0049 (
PULPROG zg30
TD 65536
SOLVENT DMSO
NS 2
DS 2
SWH 10000.000 Hz
FIDRES 0.305176 Hz
AQ 3.2767999 sec
RG 53.98
DW 50.000 usec
DE 15.00 usec
TE 293.8 K
D1 1.00000000 sec
TD0 1
SFO1 500.1630885 MHz
NUC1 1H
P1 12.00 usec
PLW1 16.64100075 W
F2 - Processing parameters
SI 65536
SF 500.1600000 MHz
WDW EM
SSB 0
LB 0.30 Hz
GB 0
PC 1.00
2.50 2.51 2.51 3.35 4.75 4.76 4.77 5.24 5.24 5.25 5.25 5.26 5.27 5.27 5.27 5.36 5.36 5.37 5.37 5.39 5.40 5.40 5.40 6.37 6.37 7.10 7.11 7.11 7.11 7.12 7.12 7.27 7.28 7.29 7.29 7.30 7.30 7.31 7.51 7.53 7.53 7.55 7.71 7.72 7.73
0.3 2.0 1.0 1.0 0.9 1.0 3.0 2.0 2.0 2.0 0.0
ppm 1 2 3 4 5 6 7 8 9
ppm 11 12 13 14 15

COPOLYMER DERIVED FROM SUBSTITUTED BENZOPINACOL AND USE OF THE SAME AS POLYMERIZATION INITIATOR

CROSS-REFERENCE TO RELATED APPLICATIONS

This application is a U.S. National Phase Application of International Patent Application No. PCT/EP2021/073385, filed Aug. 24, 2021, which claims priority to Chinese Patent Application No. PCT/CN2020/113552, filed Sep. 4, 2020, each of which is hereby incorporated by reference herein.

FIELD OF THE INVENTION

The present invention relates to a copolymer derived from a substituted benzopinacol compound, use of the copolymer as a radical polymerization initiator, and the substituted benzopinacol compound.

BACKGROUND OF THE INVENTION

Benzopinacol (i.e., 1,1,2,2-tetraphenyl-1,2-ethanediol), was well-known as a radical polymerization initiator. However, use of benzopinacol in some applications was limited by its very poor solubility in common organic solvents, especially in the applications requiring low volatile organic compound (VOC).

Modifications of benzopinacol for example, by reaction with chlorosilanes or polyorganosilane/siloxanes, by reaction with isocyanates, or by reaction with metal complex together with an alcohol have been reported, for example in U.S. Pat. No. 8,487,054. It is said that reactivity and solubility may be improved by the modification with chlorosilanes or polyorganosilane/siloxanes. However, solubilities of those modified benzopinacols in an organic solvent were not reported.

It is desirable to provide a radical polymerization initiator which may possess advantages of benzopinacol as a radical polymerization initiator, but have an increased solubility in organic solvents.

SUMMARY OF THE INVENTION

In one aspect, the present invention provides a copolymer comprising, (A) allyloxycarbonyl substituted benzopinacol monomer of formula (I)

(I)

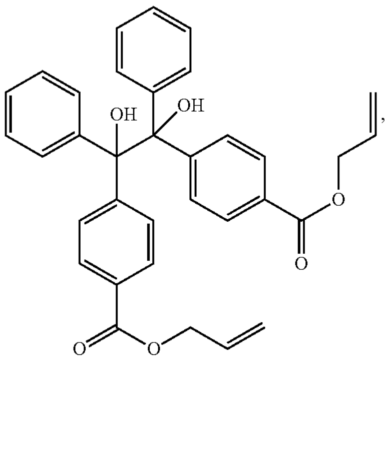

, and (B) at least one ethylenically unsaturated monomer, in copolymerized from.

In another aspect, the present invention provides use of the copolymer as described herein as a radical polymerization initiator.

In a further aspect, the present invention provides the allyloxycarbonyl substituted benzopinacol of formula (I).

It has been found by the inventors that the copolymer comprising (A) the allyloxycarbonyl substituted benzopinacol monomer of formula (I) and (B) the at least one ethylenically unsaturated monomer in copolymerized form is particularly useful as a radical polymerization initiator, which has a much higher solubility and thus is easier to handle during applications compared with the conventional small molecular benzopinacol initiator.

DETAILED DESCRIPTION OF THE INVENTION

The present invention now will be described in details hereinafter. It is to be understood that the present invention may be embodied in many different ways and shall not be construed as limited to the embodiments set forth herein. Unless mentioned otherwise, all technical and scientific terms used herein have the same meaning as commonly understood by one of ordinary skill in the art to which the present invention belongs.

Within the context of the present application, the singular forms “a”, “an” and “the” include plural referents unless the context clearly dictates otherwise.

Within the context of the present application, the terms “comprise(s)”, “comprising”, etc. are used interchangeably with “contain(s)”, “containing”, etc. and are to be interpreted in a non-limiting, open manner. That is, e.g., further components or elements may be present. The expressions “consists of” or “consists essentially of” or cognates may be embraced within “comprises” or cognates.

Within the context of the present application, when the copolymer comprising (A) allyloxycarbonyl substituted benzopinacol monomer of formula (I) and (B) at least one ethylenically unsaturated monomer is referred to, the terms “copolymer” and “copolymeric initiator” may also be used.

Within the context of the present application, when (A) allyloxycarbonyl substituted benzopinacol monomer of formula (I) is referred to, the term “comonomer (A)” may also be used.

Within the context of the present application, when (B) at least one ethylenically unsaturated monomer is referred to, the term “comonomer (B)” may also be used.

Within the context of the present application, the term (meth)acrylate stands for acrylates and/or methacrylates.

The copolymeric initiator according to the present invention comprises, (A) allyloxycarbonyl substituted benzopinacol monomer of formula (I)

(I)

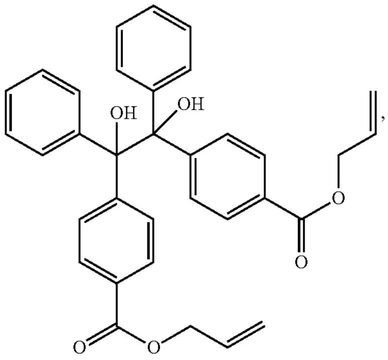

and (B) at least one ethylenically unsaturated monomer, in copolymerized from.

It is to be understood that the copolymeric initiator according to the present invention is a copolymer comprising structural units resulted from the comonomer (A) and structural units resulted from the comonomer (B) via addition copolymerization.

In some embodiments, the copolymeric initiator according to the present invention comprises the comonomer (A) and the comonomer (B) in randomly copolymerized form.

There is no particular restriction to the ethylenically unsaturated monomers as the comonomer (B). Any compounds comprising at least one olefinic double bond suitable for polymerization with the comonomer (A) may be used as the comonomer (B). For example, the ethylenically unsaturated monomers may be selected from α,β-unsaturated carboxylic acids and esters thereof, ethylenically unsaturated nitriles, vinyl esters of $C_1$-$C_{20}$-carboxylic acids, vinyl aromatics having at most 20 carbon atoms, vinyl halides, vinyl ethers of $C_1$-$C_{20}$-alcohol, $C_2$-$C_{20}$-unsaturated olefins having one or two olefinic double bonds, or any combinations thereof.

In some embodiments, the comonomer (B) comprises at least one α,β-unsaturated carboxylic acid ester. Preferably, the at least one α,β-unsaturated carboxylic acid ester is selected from $C_1$-$C_{20}$-alkyl esters of $C_3$-$C_6$-α,β-unsaturated carboxylic acids, $C_3$-$C_{12}$-cycloalkyl esters of $C_3$-$C_6$-α,β-unsaturated carboxylic acids and any combinations thereof. More preferably, the at least one α,β-unsaturated carboxylic acid ester is selected from $C_1$-$C_{20}$-alkyl (meth)acrylates, $C_3$-$C_{12}$-cycloalkyl (meth)acrylates and any combinations thereof.

Accordingly, the copolymeric initiator according to the present invention in some further embodiments comprises (A) allyloxycarbonyl substituted benzopinacol monomer of formula (I)

(I)

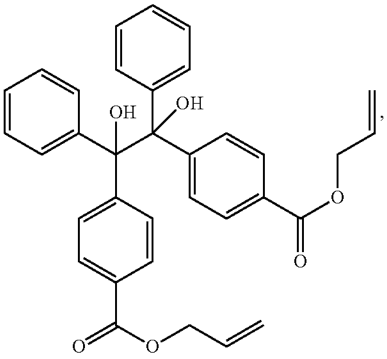

and (B) at least one ethylenically unsaturated monomer selected from $C_1$-$C_{20}$-alkyl (meth)acrylates, $C_3$-$C_{12}$-cycloalkyl (meth)acrylates and any combinations thereof, preferably $C_1$-$C_{20}$-alkyl (meth)acrylates, more preferably $C_4$-$C_{18}$-alkyl (meth)acrylates, particularly $C_4$-$C_{12}$-alkyl (meth)acrylates.

Examples of $C_1$-$C_{20}$-alkyl (meth)acrylates may include, but are not limited to, ethyl acrylate, ethyl methacrylate, propyl acrylate, propyl methacrylate, isopropyl acrylate, isopropyl methacrylate, n-butyl acrylate, n-butyl methacrylate, isobutyl acrylate, isobutyl methacrylate, tert-butyl acrylate, tert-butyl methacrylate, amyl acrylates, amyl methacrylates, hexyl acrylates, hexyl methacrylates, octyl acrylates such as 2-ethylhexyl acrylate, octyl methacrylates such as 2-ethylhexyl methacrylate, nonyl acrylates such as 3,3,5-trimethylhexyl acrylate, nonyl methacrylates such as 3,3,5-trimethylhexyl methacrylate, dodecyl acrylates such as lauryl acrylate, dodecyl methacrylates such as lauryl methacrylate, tridecyl acrylates, tridecyl methacrylates, tetradecyl acrylates, tetradecyl methacrylates, pentadecyl acrylates, pentadecyl methacrylates, hexadecyl acrylates, hexadecyl methacrylates, heptadecyl acrylates, heptadecyl methacrylates, octadecyl acrylates, octadecyl methacrylates, or any combinations thereof.

Examples of $C_3$-$C_{12}$-cycloalkyl (meth)acrylates may include, but are not limited to, cyclopentyl acrylate, cyclopentyl methacrylate, cyclohexyl acrylate, cyclohexyl methacrylate, methylcyclohexyl acrylate, methylcyclohexyl methacrylate, t-butylcyclohexyl acrylate, t-butylcyclohexyl methacrylate, isobornyl acrylate, isobornyl methacrylate, or any combinations thereof.

In some embodiments, the copolymeric initiator according to the present invention comprises (A) allyloxycarbonyl substituted benzopinacol monomer of formula (I)

(I)

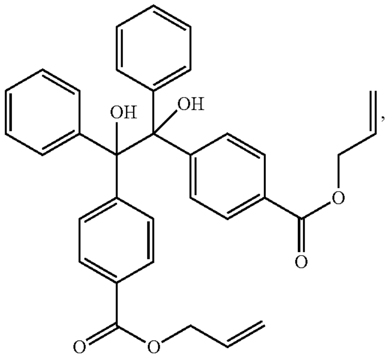

and (B) at least one ethylenically unsaturated monomer selected from n-butyl acrylate, n-butyl methacrylate, isobutyl acrylate, isobutyl methacrylate, tert-butyl acrylate, tert-butyl methacrylate, amyl acrylates, amyl methacrylates, hexyl acrylates, hexyl methacrylates, octyl acrylates such as 2-ethylhexyl acrylate, octyl methacrylates such as 2-ethylhexyl methacrylate, nonyl acrylates such as 3,3,5-trimethylhexyl acrylate, nonyl methacrylates such as 3,3,5-trimethylhexyl methacrylate, dodecyl acrylates such as lauryl acrylate, dodecyl methacrylates such as lauryl methacrylate, tridecyl acrylates, tridecyl methacrylates, tetradecyl acrylates, tetradecyl methacrylates, pentadecyl acrylates, pentadecyl methacrylates, hexadecyl acrylates, hexadecyl methacrylates, heptadecyl acrylates, heptadecyl methacrylates, octadecyl acrylates, octadecyl methacrylates and any combinations thereof.

In some further embodiments, the copolymeric initiator according to the present invention comprises (A) allyloxycarbonyl substituted benzopinacol monomer of formula (I)

(I)

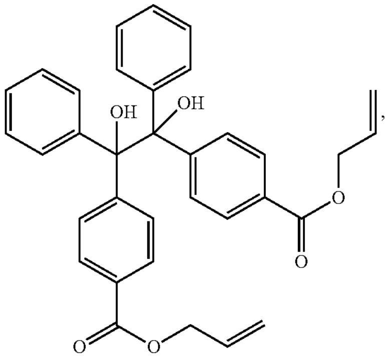

and (B) at least one ethylenically unsaturated monomer selected from n-butyl acrylate, n-butyl methacrylate, 2-ethylhexyl acrylate, 2-ethylhexyl methacrylate, lauryl acrylate, lauryl methacrylate, and any combinations thereof.

In a particular embodiment, the copolymeric initiator according to the present invention comprises (A) allyloxycarbonyl substituted benzopinacol monomer of formula (I)

(I)

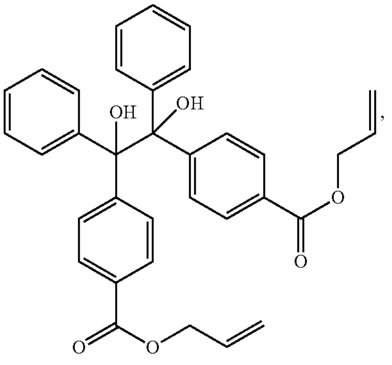

and (B) at least one of n-butyl acrylate and n-butyl methacrylate, at least one of 2-ethylhexyl acrylate and 2-ethylhexyl methacrylate, and at least one of lauryl acrylate and lauryl methacrylate.

According to any of the embodiments described herein, in the copolymeric initiators according to the present invention, total structural units from the comonomer (A) and total structural units from the comonomer (B) are comprised in a weight ratio of from 1:30 to 1:10, preferably from 1:25 to 1:15, particularly from 1:20 to 1:16.

The copolymeric initiator according to the present invention may have a number average molecular weight (Mw) in the range of from 5,000 to 500,000 g/mol, preferably from 10,000 to 200,000 g/mol, more preferably from 20,000 to 100,000 g/mol, most preferably from 30,000 to 70,000 g/mol, as measured by Gel Permeation Chromatography (GPC) in THF, with polystyrene standards.

The copolymeric initiator according to the present invention may have a weight average molecular weight (Mw) in the range of from 20,000 to 1,000,000 g/mol, preferably from 40,000 to 800,000 g/mol, more preferably from 80,000 to 500,000 g/mol, most preferably from 100,000 to 300,000 g/mol, as measured by Gel Permeation Chromatography (GPC) in THF, with polystyrene standards.

There is no particular restriction to the process for preparing the copolymeric initiator according to the present invention, which may be conducted for example by free radical polymerization, especially thermal free radical polymerization of the comonomer (A) and the comonomer (B). Any conventional process conditions such as solvents, polymerization temperatures and polymerization initiators for free radical polymerization may be used for the purpose of the present invention.

The present invention also provides a novel compound, allyloxycarbonyl substituted benzopinacol of formula (I), (I)

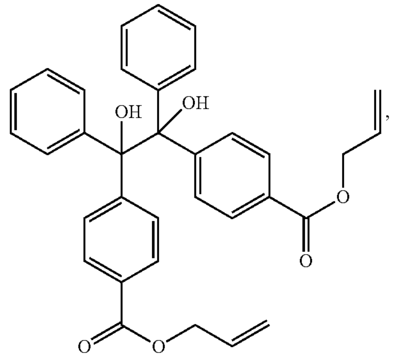

The compound of formula (I) may be prepared by subjecting allyl 4-benzoylbenzoate to a pinacol-coupling reaction. The pinacol-coupling reaction is well-known in the art and may be conducted via various processes. For example, the pinacol-coupling reaction may be conducted in the presence of a metal reductant such as Zn, Mg and Ni powder, in an aqueous solution of ammonium chloride and optionally with an inert organic solvent such as THF.

The present invention further provides use of the copolymer as described hereinabove as a radical polymerization initiator.

The copolymeric initiator may be used in various systems comprising one or more ethylenically unsaturated monomers such as (meth)acrylate and styrene functional monomers or comprising polymers containing ethylenically unsaturated functional groups such as unsaturated polyesters. It will be understood that the copolymeric initiator may be used in any systems which comprises a conventional pinacol initiator such as benzopinacol.

The copolymeric initiator is particularly useful in a coating material, for example automotive coating material, comprising a monomeric and/or oligomeric reactive diluent having at least one olefinic double bond.

EMBODIMENTS

Various embodiments are listed below. It will be understood that the embodiments listed below may be combined with all aspects and other embodiments in accordance with the scope of the invention.

Embodiment 1

A copolymer comprising, (A) allyloxycarbonyl substituted benzopinacol monomer of formula (I)

(I)

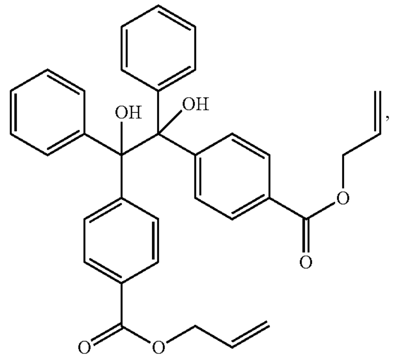

and (B) at least one ethylenically unsaturated monomer, in copolymerized from.

Embodiment 2

The copolymer according to Embodiment 1, which comprises (A) the allyloxycarbonyl substituted benzopinacol monomer of formula (I) and (B) the at least one ethylenically unsaturated monomer in randomly copolymerized form.

Embodiment 3

The copolymer according to Embodiment 1 or 2, wherein (B) the at least one ethylenically unsaturated monomer is selected from α,β-unsaturated carboxylic acids and esters thereof, ethylenically unsaturated nitriles, vinyl esters of $C_1$-$C_{20}$-carboxylic acids, vinyl aromatics having at most 20 carbon atoms, vinyl halides, vinyl ethers of $C_1$-$C_{20}$-alcohol, $C_2$-$C_{20}$-unsaturated olefins having one or two olefinic double bonds, and any combinations thereof.

Embodiment 4

The copolymer according to any of Embodiments 1 to 3, wherein (B) the at least one ethylenically unsaturated monomer comprises at least one α,β-unsaturated carboxylic acid ester, for example $C_1$-$C_{20}$-alkyl esters of $C_3$-$C_6$-α,β-unsaturated carboxylic acids, $C_3$-$C_{12}$-cycloalkyl esters of $C_3$-$C_6$-α,β-unsaturated carboxylic acids or any combinations thereof, particularly $C_1$-$C_{20}$-alkyl (meth)acrylates, $C_3$-$C_{12}$-cycloalkyl (meth)acrylates or any combinations thereof.

Embodiment 5

The copolymer according to any of Embodiments 1 to 4, wherein (B) the at least one ethylenically unsaturated monomer is selected from $C_1$-$C_{20}$-alkyl (meth)acrylates, $C_3$-$C_{12}$-cycloalkyl (meth)acrylates and any combinations thereof, preferably selected from $C_1$-$C_{20}$-alkyl (meth)acrylates, more preferably $C_4$-$C_{18}$-alkyl (meth)acrylates, particularly $C_4$-$C_{12}$-alkyl (meth)acrylates.

Embodiment 6

The copolymer according to any of Embodiments 1 to 5, wherein (B) the at least one ethylenically unsaturated monomer is selected from n-butyl acrylate, n-butyl methacrylate, isobutyl acrylate, isobutyl methacrylate, tert-butyl acrylate, tert-butyl methacrylate, amyl acrylates, amyl methacrylates, hexyl acrylates, hexyl methacrylates, octyl acrylates such as 2-ethylhexyl acrylate, octyl methacrylates such as 2-ethylhexyl methacrylate, nonyl acrylates such as 3,3,5-trimethylhexyl acrylate, nonyl methacrylates such as 3,3,5-trimethylhexyl methacrylate, dodecyl acrylates such as lauryl acrylate, dodecyl methacrylates such as lauryl methacrylate, tridecyl acrylates, tridecyl methacrylates, tetradecyl acrylates, tetradecyl methacrylates, pentadecyl acrylates, pentadecyl methacrylates, hexadecyl acrylates, hexadecyl methacrylates, heptadecyl acrylates, heptadecyl methacrylates, octadecyl acrylates, octadecyl methacrylates, and any combinations thereof.

Embodiment 7

The copolymer according to any of Embodiments 1 to 6, wherein (B) the at least one ethylenically unsaturated monomer is selected from n-butyl acrylate, n-butyl methacrylate, 2-ethylhexyl acrylate, 2-ethylhexyl methacrylate, lauryl acrylate, lauryl methacrylate, and any combinations thereof.

Embodiment 8

The copolymer according to any of Embodiments 1 to 7, which comprises (A) allyloxycarbonyl substituted benzopinacol monomer of formula (I)

(I)

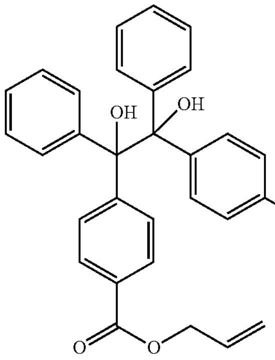

and (B) at least one of n-butyl acrylate and n-butyl methacrylate, at least one of 2-ethylhexyl acrylate and 2-ethylhexyl methacrylate, and at least one of lauryl acrylate and lauryl methacrylate.

Embodiment 9

The copolymer according to any of Embodiments 1 to 8, wherein total structural units from the comonomer (A) and total structural units from the comonomer (B) are comprised in a weight ratio of from 1:30 to 1:10, preferably from 1:25 to 1:15, particularly from 1:20 to 1:16.

Embodiment 10

The copolymer according to any of Embodiments 1 to 9, which has a number average molecular weight (Mn) in the range of from 5,000 to 500,000 g/mol, preferably from 10,000 to 200,000 g/mol, more preferably from 20,000 to 100,000 g/mol, most preferably from 30,000 to 80,000 g/mol.

Embodiment 11

The copolymer according to any of Embodiments 1 to 10, which has a weight average molecular weight (Mw) in the range of from 20,000 to 1,000,000 g/mol, preferably from 40,000 to 800,000 g/mol, more preferably from 80,000 to 500,000 g/mol, most preferably from 100,000 to 300,000 g/mol.

Embodiment 12

The copolymer according to any of Embodiments 1 to 11, which is obtainable or obtained by free radical polymerization, especially thermal free radical polymerization.

Embodiment 13

Use of the copolymer according to any of Embodiments 1 to 12 as a radical polymerization initiator.

Embodiment 14

Use according to Embodiment 13 in coating material, for example automotive coating material, comprising a monomeric and/or oligomeric reactive diluent having at least one olefinic double bond.

Embodiment 15

An allyloxycarbonyl substituted benzopinacol of formula (I), (I)

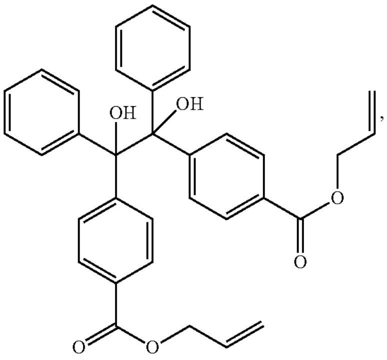

EXAMPLES

The present invention will be further described by Examples which are not intended to limit the scope of the present invention.

Example 1: Synthesis of Allyloxycarboxyl Substituted Benzopinacol of Formula (I)

1.1 Synthesis of Allyl 4-Benzoyl Benzoate

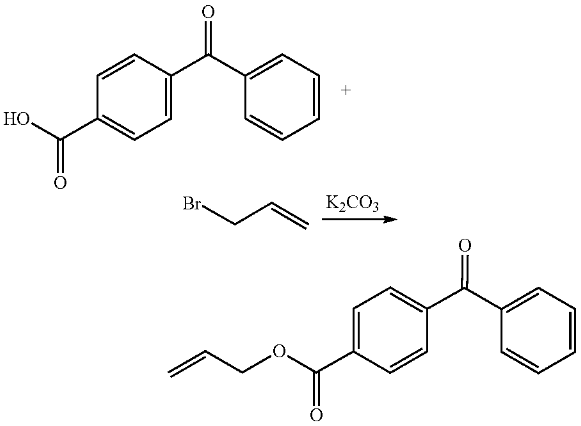

In a 100 mL round bottom flask, 49 mL of N,N-dimethyl formamide (DMF), 4.87 g of 4-benzoylbenzoic acid (0.0215 moles), 4.3 g of potassium carbonate (0.0323 moles) and 3.9 g of allyl bromide (0.0323 moles) were added and then reacted at 65° C. for 5 h under stirring. After purification by column chromatography with a mobile phase of 1.5% methyl tert-butyl ether in chloroform, allyl 4-benzoylbenzoate was obtained in a yield of 5.3 g.

1.2 Coupling of Allyl 4-Benzoylbenzoate

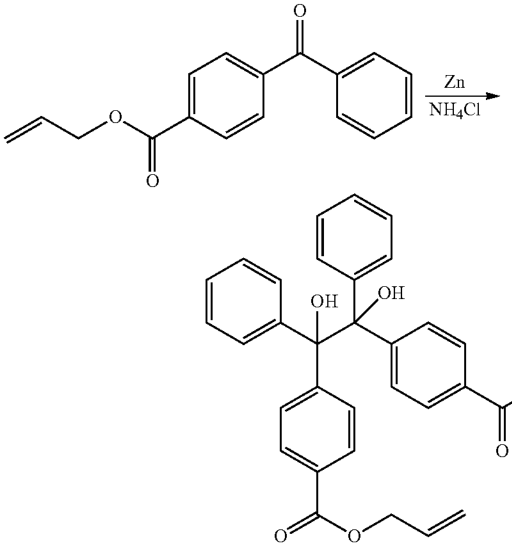

(I)

In a 1 L round bottom flask, 262 mL of tetrahydrofuran, 26.2 g of allyl 4-benzoylbenzoate (0.0983 moles), 19.28 g of Zn powder (0.295 moles) and 184 mL of 30% aqueous ammonium hydrochloride were added and heated to reflux under stirring for 6 hours. After purification by column chromatography with a mobile phase of 1.5% methyl tert-butyl ether in chloroform, the compound of formula (I) was obtained in a yield of 3.28 g.

$^1$H NMR (500 MHz, DMSO-d6, TMS): δ H=4.75-4.77 (t, 2H), 5.24-5.27 (dd, 1H), 5.36-5.40 (dd, 1H), 6.00 (m, 1H), 6.37 (s, 1H), 7.10-7.12 (t, 3H), 7.27-7.31 (m, 2H), 7.51-7.55 (t, 2H), 7.71-7.73 (m, 2H). The 1H NMR spectra is shown in FIG. 1.

Example 2: Synthesis of Copolymeric Initiator

Into a 100 mL 3-neck flask equipped with a nitrogen inlet connection, 10 g of solvent naphtha 160/180 was added and heated to 80° C. A solution of 0.5 g of the compound of formula (I), 3 g of 2-ethylhexyl acrylate, 3 g of n-butyl acrylate and 3 g of lauryl acrylate dissolved in 25 g chloroform was dosed into the flask over 3.25 hours under stirring; meanwhile a solution of 0.2 g of tertbutyl peroxy-2-ethylhexanoate dissolved in 2 g of solvent naphtha 160/180 was dosed into the flask over 3.5 hours. After all dosages were completed, the reaction system was kept under the same temperature for 1 hour under stirring, and then cooled down to finish the polymerization. The whole process was carried out with nitrogen purging. A transparent viscous polymer solution was obtained. Conversion of the compound of formula (I) as determined by liquid chromatography was 92%.

As measured by GPC in THF with polystyrene standards, the resulted polymer has a number average molecular weight (Mn) of 55,200 g/mol and a weight average molecular weight (Mw) of 218,000 g/mol, and has a PDI of 3.95.

Example 3: Test of Polymerization Performance 3.1 Preparation of Polymerization System with the Copolymeric Initiator The transparent viscous polymer solution as obtained from Example 2 was vacuumed to remove part of solvents to provide a polymer solution having a solid content of 50% as measured in accordance with GB 24409-2020. The obtained polymer solution was used as the copolymeric initiator system. The benzopinacol structural units account for 2.5 wt % of the total weight of the copolymeric initiator system. The solvent of the copolymeric initiator system consists of 12.2 wt % chloroform and 87.8 wt % solvent naphtha as determined by gas chromatography.

A monomer solution was prepared by mixing 90 g of trimethylolpropane triacrylate (TMPTA) and 2 g of butyl glycol under stirring. 4 g of the copolymeric initiator system was added into the monomer solution and stirred under room temperature for 1 hour. The resulted mixture was a transparent and clear solution, which was to be used as the polymerization system.

3.2 Preparation of Polymerization System with Benzopinacol

A monomer solution was prepared by mixing 90 g of TMPTA, 2 g of butyl glycol, 0.24 g of chloroform and 1.76 g solvent naphtha 160/180 under stirring. 1 g of benzopinacol fine powder was added into the monomer solution and stirred under room temperature for 1 hour. The resulted mixture was a transparent liquid with suspended fine particles and was to be used as the polymerization system.

3.3 Preparation of Polymerization System with Benzopinacol

A monomer solution was prepared by mixing 90 g of TMPTA and 10 g of butyl glycol under stirring. 1 g of fine benzopinacol fine powder was added into the monomer solution and stirred under room temperature for 1 hour. The resulted mixture was a transparent liquid with suspended fine particles and was to be used as the polymerization system.

3.4 Preparation of Polymerization System with the Compound of Formula (I)

A monomer solution was prepared by mixing 90 g of TMPTA and 10 g of butyl glycol by stirring. 1 g of the compound of formula (I) was added into the monomer solution and stirred under room temperature for 1 hour. The resulted mixture was a transparent liquid with suspended fine particles and was to be used as the polymerization system.

The polymerization systems were measured with a dynamic thermomechanical analyzer (HAAKE Viscotester iQ Air rheometer) to characterize the initiation performance of the initiators. The measurement was operated under OSC mode with a heating rate of 4.67° C./min. On-set temperature was determined from the measured curve as indicator of the initiation performance. The test results were summarized in Table 1.

TABLE 1

| Polymerization system | Example 3.1[a)] | Example 3.2[b)] | Example 3.3[c)] | Example 3.4[d)] |
|---|---|---|---|---|
| On-set Temperature (° C.) | 118 | 134 | 118 | 121 |

[a)]Initiator: inventive copolymer; Solvent: 2 g of butyl glycol, 0.24 g of chloroform and 1.76 g solvent naphtha

[b)]Initiator: benzopinacol; Solvent: 2 g of butyl glycol, 0.24 g of chloroform and 1.76 g solvent naphtha

[c)]Initiator: benzopinacol; Solvent: 10 g butyl glycol

[d)]Initiator: substituted benzopinacol of formula (I); Solvent: 10 g butyl glycol It can be seen that the polymerization system of Example 3.1 using the inventive copolymeric initiator shows a much lower on-set temperature than that of the polymerization system of Example 3.2 using benzopinacol, under the same solvent composition. The on-set temperature of the polymerization system using benzopinacol was decreased at a much higher solvent amount as shown via comparison between the polymerization systems of Example 3.2 and Example 3.3. It is believed that the poor solubility of benzopinacol result in the inferior initiation efficiency, and thus is responsible for the higher on-set temperature of the polymerization system of Example 3.2.

Although benzopinacol may provide suitable initiation performance in a polymerization system containing a sufficient amount of solvent, high amount of solvent will cause undesirable VOC and may require long dissolving process and additional treatment process such as filtration. The solubility deficiency of benzopinacol was not remedied in case of allyloxycarbonyl substituted benzopinacol, which even has a worse initiation performance compared with benzopinacol as can be seen from the test result of the polymerization system of Example 3.4. On the contrary, desirable initiation performance has been achieved by the inventive copolymeric initiator, while low amount of organic solvent is required and the process is simplified.

The invention has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

The invention claimed is:

1. A copolymer comprising, (A) allyloxycarbonyl substituted benzopinacol monomer of formula (I)

(I)

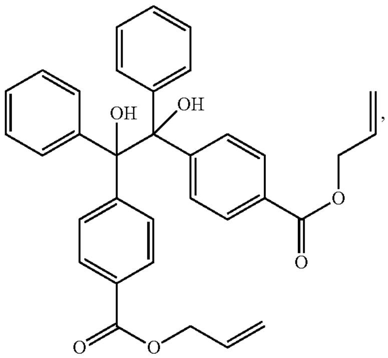

and (B) at least one ethylenically unsaturated monomer, in copolymerized form.

2. The copolymer according to claim 1, which comprises (A) the allyloxycarbonyl substituted benzopinacol monomer of formula (I) and (B) the at least one ethylenically unsaturated monomer in randomly copolymerized form.

3. The copolymer according to claim 1, wherein (B) the at least one ethylenically unsaturated monomer is selected from the group consisting of α,β-unsaturated carboxylic acids and esters thereof, ethylenically unsaturated nitriles, vinyl esters of $C_1$-$C_{20}$-carboxylic acids, vinyl aromatics having at most 20 carbon atoms, vinyl halides, vinyl ethers of $C_1$-$C_{20}$-alcohol, $C_2$-$C_{20}$-unsaturated olefins having one or two olefinic double bonds, and any combinations thereof.

4. The copolymer according to claim 1, wherein (B) the at least one ethylenically unsaturated monomer comprises at least one α,β-unsaturated carboxylic acid ester.

5. The copolymer according to claim 1, wherein (B) the at least one ethylenically unsaturated monomer is selected from the group consisting of $C_1$-$C_{20}$-alkyl esters of $C_3$-$C_6$-α,β-unsaturated carboxylic acids, $C_3$-$C_{12}$-cycloalkyl esters of $C_3$-$C_6$-α,β-unsaturated carboxylic acids, $C_1$-$C_{20}$-alkyl (meth)acrylates, $C_3$-$C_{12}$-cycloalkyl (meth)acrylates and any combinations thereof.

6. The copolymer according to claim 1, wherein (B) the at least one ethylenically unsaturated monomer is selected from the group consisting of n-butyl acrylate, n-butyl methacrylate, isobutyl acrylate, isobutyl methacrylate, tert-butyl acrylate, tert-butyl methacrylate, amyl acrylates, amyl methacrylates, hexyl acrylates, hexyl methacrylates, octyl acrylates, 2-ethylhexyl acrylate, octyl methacrylates, 2-ethylhexyl methacrylate, nonyl acrylates, 3,3,5-trimethylhexyl acrylate, nonyl methacrylates, 3,3,5-trimethylhexyl methacrylate, dodecyl acrylates, lauryl acrylate, dodecyl methacrylates, lauryl methacrylate, tridecyl acrylates, tridecyl methacrylates, tetradecyl acrylates, tetradecyl methacrylates, pentadecyl acrylates, pentadecyl methacrylates, hexadecyl acrylates, hexadecyl methacrylates, heptadecyl acrylates, heptadecyl methacrylates, octadecyl acrylates, octadecyl methacrylates, and any combinations thereof.

7. The copolymer according to claim 1, wherein (B) the at least one ethylenically unsaturated monomer is selected from the group consisting of n-butyl acrylate, n-butyl methacrylate, 2-ethylhexyl acrylate, 2-ethylhexyl methacrylate, lauryl acrylate, lauryl methacrylate, and any combinations thereof.

8. The copolymer according to claim 1, which comprises (A) allyloxycarbonyl substituted benzopinacol monomer of formula (I)

(I)

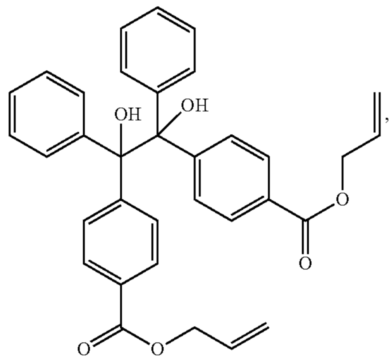

and (B) at least one of n-butyl acrylate and n-butyl methacrylate, at least one of 2-ethylhexyl acrylate and 2-ethylhexyl methacrylate, and at least one of lauryl acrylate and lauryl methacrylate.

9. The copolymer according to claim 1, wherein total structural units from the comonomer (A) and total structural units from the comonomer (B) are comprised in a weight ratio of from 1:30 to 1:10.

10. The copolymer according to claim 1, which has a number average molecular weight (Mn) in the range of from 5,000 to 500,000 g/mol.

11. The copolymer according to claim 1, which has a weight average molecular weight (Mw) in the range of from 20,000 to 1,000,000 g/mol.

12. The copolymer according to claim 1, which is obtainable or obtained by free radical polymerization.

13. A method comprising performing a radical polymerization reaction in the presence of the copolymer of claim 1 as a radical polymerization initiator.

14. The method according to claim 13, comprising radical polymerizing a monomeric and/or an oligomeric reactive diluent having at least one olefinic double bond in the presence of the copolymer, to form a coating material.

15. An allyloxycarbonyl substituted benzopinacol of formula (I), (I)

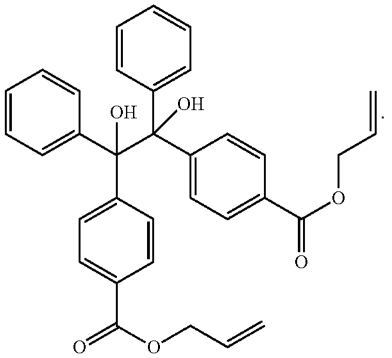

16. The copolymer according to claim 1, wherein (B) the at least one ethylenically unsaturated monomer is selected from the group consisting of $C_1$-$C_{20}$-alkyl (meth)acrylates.

17. The copolymer according to claim 1, wherein (B) the at least one ethylenically unsaturated monomer is selected from the group consisting of $C_4$-$C_{18}$-alkyl (meth)acrylates.

18. The copolymer according to claim 1, wherein (B) the at least one ethylenically unsaturated monomer is selected from the group consisting of $C_4$-$C_{12}$-alkyl (meth)acrylates.

19. The copolymer according to claim 1, wherein total structural units from the comonomer (A) and total structural units from the comonomer (B) are comprised in a weight ratio of from 1:25 to 1:15.

20. The copolymer according to claim 1, wherein total structural units from the comonomer (A) and total structural units from the comonomer (B) are comprised in a weight ratio of from 1:20 to 1:16.

* * * * *